(12) United States Patent
Geier et al.

(10) Patent No.: US 7,454,949 B2
(45) Date of Patent: Nov. 25, 2008

(54) GAS SENSOR AND METHOD FOR PRODUCTION THEREOF

(75) Inventors: Heinz Geier, Leonberg (DE); Helmut Weyl, Wiesbaden (DE); Siegfried Nees, Neckarwestheim (DE); Bernhard Wild, Markgroeningen (DE); Rainer Maier, Tamm (DE); Michael Liebler, Leonberg (DE); Peter Dettling, Waiblingen (DE); Bettina Schneider, Ludwigsburg (DE); Craig Magera, Simpsonville, SC (US)

(73) Assignee: Robert Bosch GmbH, Stuttgart (DE)

( * ) Notice: Subject to any disclaimer, the term of this patent is extended or adjusted under 35 U.S.C. 154(b) by 110 days.

(21) Appl. No.: 10/516,723

(22) PCT Filed: May 15, 2003

(86) PCT No.: PCT/DE03/01578

§ 371 (c)(1),
(2), (4) Date: Jan. 17, 2006

(87) PCT Pub. No.: WO03/104791

PCT Pub. Date: Dec. 18, 2003

(65) Prior Publication Data

US 2006/0162422 A1      Jul. 27, 2006

(30) Foreign Application Priority Data

Jun. 6, 2002   (DE) ............................. 102 25 150

(51) Int. Cl.
*G01N 27/04*   (2006.01)
*G01N 27/407*  (2006.01)
*H01C 7/00*    (2006.01)
*G01M 15/00*   (2006.01)

(52) U.S. Cl. .................. 73/23.31; 73/31.05; 204/424
(58) Field of Classification Search ............. 73/23.31, 73/23.32, 31.05, 31.06; 204/424, 425, 426, 204/427, 728, 429
See application file for complete search history.

(56) References Cited

U.S. PATENT DOCUMENTS

| 5,031,445 | A  | * | 7/1991  | Kato et al. ............... 73/23.31 |
| 5,329,806 | A  | * | 7/1994  | McClanahan et al. ...... 73/31.05 |
| 5,616,825 | A  | * | 4/1997  | Achey et al. ............. 73/23.31 |
| 5,739,414 | A  | * | 4/1998  | Paulus et al. ............ 73/23.31 |
| 5,955,656 | A  | * | 9/1999  | Graser et al. ............ 73/23.31 |
| 6,266,997 | B1 | * | 7/2001  | Nelson .................... 73/31.05 |
| 6,319,376 | B1 | * | 11/2001 | Graser et al. ............ 204/424 |
| 6,327,891 | B1 | * | 12/2001 | Noda et al. .............. 73/31.05 |
| 6,347,543 | B1 | * | 2/2002  | Geier et al. ............. 73/23.31 |

(Continued)

FOREIGN PATENT DOCUMENTS

DE      197 07 456      8/1998

(Continued)

*Primary Examiner*—Michael Cygan
(74) *Attorney, Agent, or Firm*—Kenyon & Kenyon LLP

(57) ABSTRACT

A gas sensor, whose purpose is to determine a physical property of a measuring gas, e.g., to determine the concentration of a gas component or the temperature of an exhaust gas. The gas sensor includes a sensor element arranged in a metal housing which is sealed by at least one sealing element arranged in a metal receptacle. The metal receptacle is affixed to the housing. The sealing element surrounds the sensor element in a centered position along its longitudinal extension L or on its half facing the measuring gas.

15 Claims, 4 Drawing Sheets

U.S. PATENT DOCUMENTS 6,418,777 B1 * 7/2002 Noda et al. ................. 73/23.2
6,453,726 B1 * 9/2002 Gutierrez et al. ........... 73/31.05
6,474,655 B1 * 11/2002 Weyl et al. .................. 277/650
6,550,309 B1 * 4/2003 Noda et al. ................. 73/31.05
6,673,224 B2 * 1/2004 Shirai ......................... 204/427
6,758,082 B2 * 7/2004 Geier et al. ................. 73/31.05

FOREIGN PATENT DOCUMENTS

| JP | 11248673 | 9/1999 |
|----|----------|--------|
| JP | 2000514927 | 11/2000 |

* cited by examiner

GAS SENSOR AND METHOD FOR PRODUCTION THEREOF

FIELD OF THE INVENTION

The present invention relates to a gas sensor.

BACKGROUND INFORMATION

A gas sensor of this type is discussed, for example, in German Published Patent Application No. 197 07 456. The gas sensor includes a metal housing in which two molded ceramic parts are positioned axially one behind the other, which include openings for receiving a sensor element. Between the molded ceramic parts is an intermediate space, in which a glass seal that surrounds the sensor element is provided. The molded ceramic part is sealed in the housing by a sealing ring.

The gas sensor discussed in German Published Patent Application No. 197 07 456 provides that when a seal is introduced into a molded ceramic part, the danger of cracking is high due to temperature fluctuations during operation of the gas sensor. In addition, the sealing between the molded ceramic part and the housing requires complex manufacturing technology.

German Published Patent Application No. 197 51 424 discusses a gas sensor including a metal housing in which a molded ceramic part including a recess for receiving a sensor element is arranged. The molded ceramic part encircles the sensor element in its center. The end of the sensor element facing the measuring gas includes one or more measuring elements, e.g., electrochemical cells. At the end of the sensor element facing away from the measuring gas, contact surfaces, which are connected electrically by contacting with conductor elements leading out of the gas sensor, are arranged on the sensor element. Between the molded ceramic part and the end of the sensor element facing the contacting, the sensor element is enclosed by a glass seal. The glass seal is positioned in a metal receptacle which is affixed to the housing by a welded connection. The metal receptacle, the end of the sensor element facing the contacting, and the contacting are surrounded by a metal sleeve, which in turn is connected to the housing by an additional welded connection.

To produce the sensor elements for such gas sensors, ceramic sheets imprinted with functional layers are laminated together and sintered. During sintering, the ceramic sheets shrink. In this process, slight warping of the sensor elements is often unavoidable. The recess of the molded ceramic part for receiving the sensor element is therefore dimensioned so that the sensor element has play in the recess. Since the sensor element is fixed only at its end facing the contacting by a positive material connection, the sensor element is able to vibrate in the recess due to the vibrations that occur in operation, which may result in damage to the sensor element. Furthermore, building the sensor element into the rigid molded ceramic part is complex, requires difficult production techniques, and may damage the sensor element.

SUMMARY

The gas sensor according to the present invention and the method according to the present invention for producing the gas sensor provide that a sensor element is sealed in a housing using at least one sealing element in a cost-effective manner involving simple production technology, the sensor element being unaffected by vibrations that occur during operation. To this end, the sealing element is placed in a metal receptacle, which in turn is affixed to the metal housing, and the sealing element encloses the sensor element centered along a longitudinal extension L or on the side facing the measuring gas.

The sensor element is held primarily by the sealing element in the metal receptacle (as well as to a lesser degree by the contacting). This eliminates the need for one molded ceramic part, so that the metal receptacle may be exposed directly to the measuring gas.

The sealing element may include glass or glass ceramic, and forms a positive material connection with the sensor element and the molded metal part. A glass seal or a glass ceramic seal is able to adapt itself to the shape of the sensor element. This makes it possible to hold even warped sensor elements securely. To prevent mechanical stresses under temperature fluctuations, the expansion coefficient of the sealing element and the expansion coefficient of the sensor element differ by no more than 10 percent.

The glass or the glass ceramic is introduced into the receptacle for example as a powder filling, in the form of a pre-pressed or fused glass pellet or in the form of a pre-pressed powder mixture in tablet form. The glass contains a glass-forming component; the glass ceramic includes a ceramic component and a glass-forming component, for example in the form of a ceramic powder and a glass-forming powder. During a subsequent heat treatment, the glass-forming component of the glass or of the glass ceramic melts and forms a positive material connection with the surrounding materials.

The metal receptacle may be affixed to the housing by a positive material connection, e.g., by laser welding. Furthermore, on the side of the gas sensor facing away from the measuring gas, there is a sleeve that surrounds a section of the sensor element and the contacting of the sensor element. The metal receptacle and the sleeve are affixed to the housing by a common positive material connection. Especially favorable here in regard to production technology is a welded connection, e.g., a circumferential weld produced by laser welding.

The metal receptacle may be cup-shaped, the bottom of the cup-shaped metal receptacle including a recess for receiving the sensor element. At its open end the metal receptacle includes a section extending outward perpendicular to the longitudinal axis of the metal receptacle, to which an additional sleeve-shaped section is connected, so that the metal receptacle includes a collar-like expansion. The outer sleeve-shaped section of this collar-like expansion is affixed to the housing by laser welding.

An especially simple and cost-effective manufacture of the gas sensor is possible if the space from the sensor element to the side wall of the cup-shaped metal receptacle is less than or equal to twice the height of the sensor element at least in some places. The height of the sensor element refers to the extension of the sensor element perpendicular to its large surface.

In a first further development of the present invention, the metal receptacle contains a first and a second sealing element. The two sealing elements contain glass or glass ceramic as their main component, and are placed one behind the other in the receptacle in the longitudinal direction of the sensor element. The glass-forming component of the first sealing element, which faces the measuring gas, has a higher melting point than the glass-forming component of the second sealing element, which faces away from the measuring gas. When the sensor element is installed, the composite of metal receptacle, first and second sealing element, and sensor element is heated to a temperature at which the glass-forming component of the second sealing element completely melts, while the glass-forming component of the first sealing element does not melt or does not do so completely. This configuration of the sealing elements results in the second sealing element forming a gas-tight, positive material connection to the sensor element and metal receptacle, and the first sealing element preventing the glass of the second sealing element from being able to flow out of the receptacle. The configuration may also provide for the second sealing element to be positioned between the first sealing element and a third sealing element, the third sealing element having a viscous consistency at the temperatures at which the gas sensor is used. This configuration of the sealing elements reduces the risk of the glass or the glass ceramic cracking and the risk of the sensor element breaking in the area of the transition from the glass or the glass ceramic to the air.

In a second further development of the present invention, the metal receptacle includes a first and a second sealing element, which are positioned in the receptacle, one behind the other in the longitudinal direction of the sensor element. The first sealing element, which faces the measuring gas, contains a sintered ceramic, and the second sealing element, which faces away from the measuring gas, contains a glass or a glass ceramic. The first sealing element prevents the glass or the glass ceramic of the second sealing element from flowing out of the ceramic receptacle during manufacturing of the gas sensor. In addition, a wafer of pressed ceramic powdered material may be provided between the first and second sealing element as a third sealing element.

To produce the gas sensor according to the present invention, the sensor element and a sealing element or a plurality of sealing elements are placed in the metal receptacle and subjected to a heat treatment, during which the glass-forming component of at least one sealing element melts, so that the sensor element is sealed in a gas-tight manner in the metal receptacle by the sealing element. The composite of metal receptacle, sealing element, and sensor element is subsequently placed in the housing and the metal receptacle is fixed in the housing.

BRIEF DESCRIPTION OF THE DRAWINGS

FIG. 2a shows a section of a metal receptacle of the first exemplary embodiment corresponding to cut line IIa-IIa in FIG. 2b.

FIG. 2b shows a top view of the metal receptacle according to FIG. 2a.

FIG. 4a shows a section of a metal receptacle corresponding to cut line IVa-IVa in FIG. 4b.

FIG. 4b shows a top view of the metal receptacle according to FIG. 4a.

DETAILED DESCRIPTION

Figure 1:
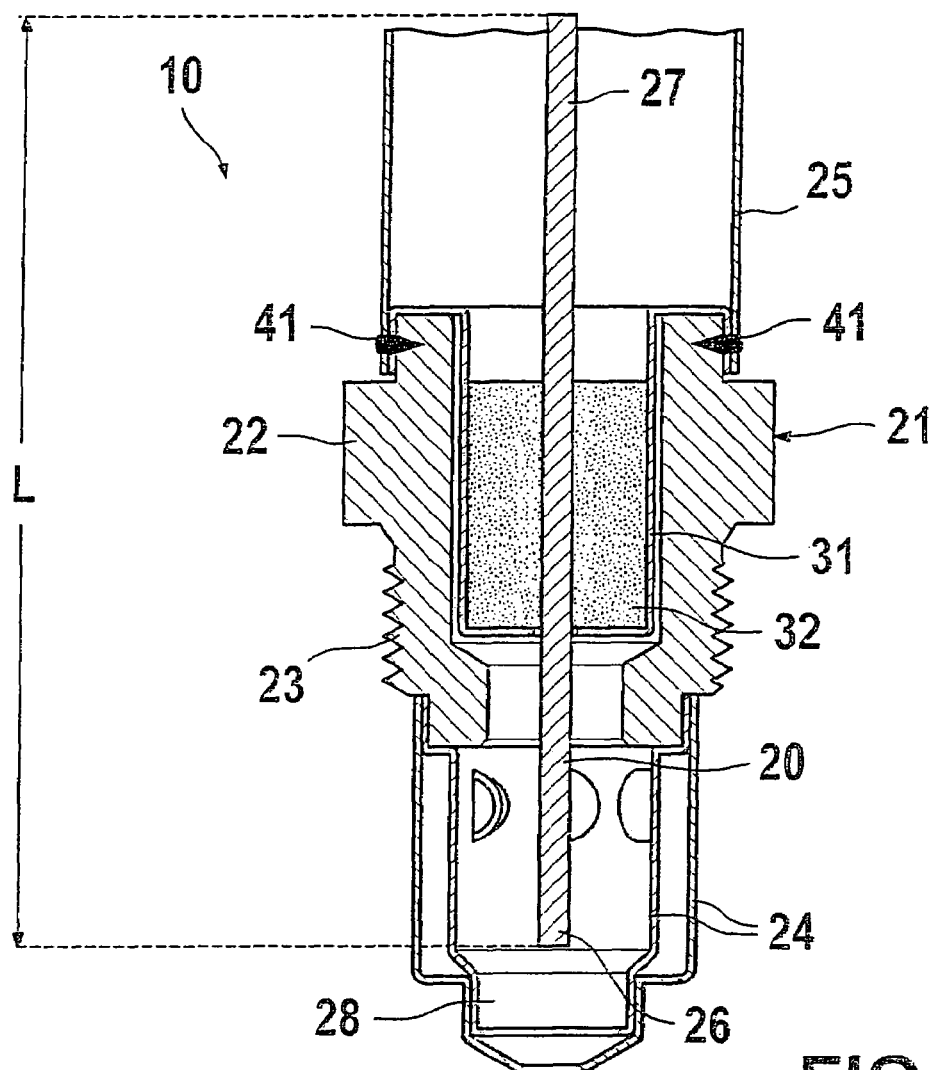
FIG. 1 shows a sectional view of a first exemplary embodiment of a gas sensor according to the present invention.

FIG. 1 shows a section of a gas sensor 10 as a first exemplary embodiment of the present invention. Gas sensor 10 is used for example to determine the temperature or the oxygen content of a measuring gas, and may be built into a measuring opening of an exhaust line of a combustion engine (not shown). Gas sensor 10 exhibits a housing 21 including threading 23 and a hexagon 22 for this purpose. Housing 21 encloses a planar, elongated sensor element 20, which is configured as a ceramic multi-layer system. On a first section 26, which is exposed to the measuring gas, sensor element 20 includes measuring elements such as electrodes or heaters. First section 26 of sensor element 20 protrudes from housing 21 into a measuring gas chamber 28, which is surrounded by a protection tube 24 affixed to housing 21. Protection tube 24 includes openings (no reference numeral) which may allow the measuring gas to access first section 26 of sensor element 20.

Contact points (not shown) are provided in a second section 27 of sensor element 20, which is separated from the measuring gas, on the outer surfaces of sensor element 20. The contact points are electrically connected to the measuring elements by connecting leads located in the composite of layers of sensor element 20. The contact points are in electrical contact via a contacting device with conducting elements (not shown), through which the measuring elements are connected to an evaluation circuit provided outside of sensor element 20. Second section 27 of sensor element 20 and the contacting device are surrounded by a sleeve 25, which is affixed to housing 21. FIGS. 1, 3, and 5 through 8 show a section of sleeve 25.

Figures 2A, 2B:
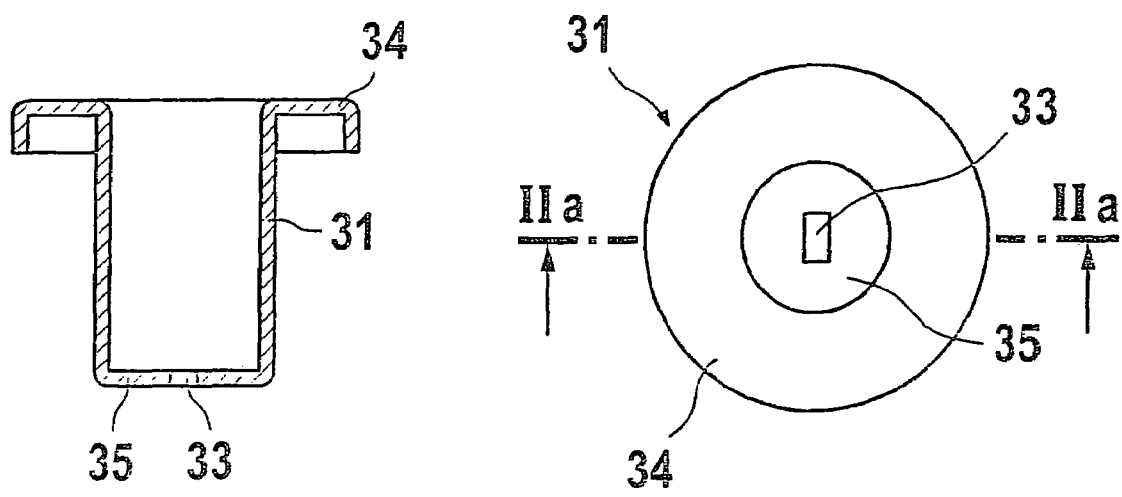

A sealing element 32, which is positioned in a metal receptacle 31 for sealing element 32, is provided for sealing first section 26 from second section 27 of sensor element 20. Metal receptacle 31 is represented in FIGS. 2a and 2b as a single element. Sealing element 32 encloses a longitudinal section of sensor element 20. This longitudinal section is provided in the middle of sensor element 20 (in reference to its longitudinal extension L), or on the half of sensor element 20 that faces the measuring gas. Sealing element 32 thus also functions as a holder for sensor element 20, and prevents sensor element 20 from vibrating in housing 21.

Sealing element 32 includes a glass or a glass ceramic and is introduced into metal receptacle 31 in the form of a glass powder or a mixture of a ceramic powder (ceramic component) and a glass-forming powder (glass-forming component). The glass powder or glass-forming powder is based chiefly on the oxides $BaO$, $SrO$, $ZnO$, $B_2O_3$, $Al_2O_3$, $MgO$, $CaO$, and/or $SiO_2$. The ceramic powder includes, for example, statite, forsterite, $Al_2O_3$, $Al_2O_3 \cdot MgO$, or $ZrO_2$ stabilized with $CaO$, $MgO$, or $Y_2O_3$, or mixtures thereof.

The source material for sealing element 32 is introduced as a powder filling into metal receptacle 31 with sensor element 20 and mechanically compacted. Alternatively, the source material may be introduced together with sensor element 20 into receptacle 31 as a pre-pressed or fused glass pellet or as a pre-pressed powder mixture in tablet form, the glass pellet or pre-pressed powder mixture including a recess for receiving sensor element 20.

In the subsequent thermal treatment of the pre-assembled composite of sensor element 20, sealing element 32 and metal receptacle 31, the glass-forming component of the glass or the glass ceramic melts, so that a gas-tight connection is formed between sensor element 20 and sealing element 32 and between metal receptacle 31 and sealing element 32. In this process, partial or complete crystallization of the glass or of the glass-forming components is producible via deliberate temperature management, so that sealing element 32 exists after the temperature treatment as a partially or fully crystallized glass ceramic.

Metal receptacle 31 is cup-shaped. Bottom 35 of metal receptacle 31 includes in its center a recess 33 for sensor element 20. Recess 33 is rectangular in shape, corresponding to the cross section of sensor element 20. The space between sensor element 20 and receptacle 31 is sufficiently small in the area of recess 33 to prevent sealing element 32 from flowing out during the melting process. Provided at the open end of receptacle 31 is a collar 34, which may be placed on housing 21. Collar 34 encircles housing 21 on its side away from the measuring gas, and is encircled in turn by sleeve 25. Sleeve 25 and collar 34 are affixed to housing 21 by a common circumferential weld.

Measuring gas chamber 28 is bounded by receptacle 31 and by protective tube 24. Sensor element 20 is the only element in measuring gas chamber 28.

Figure 3:
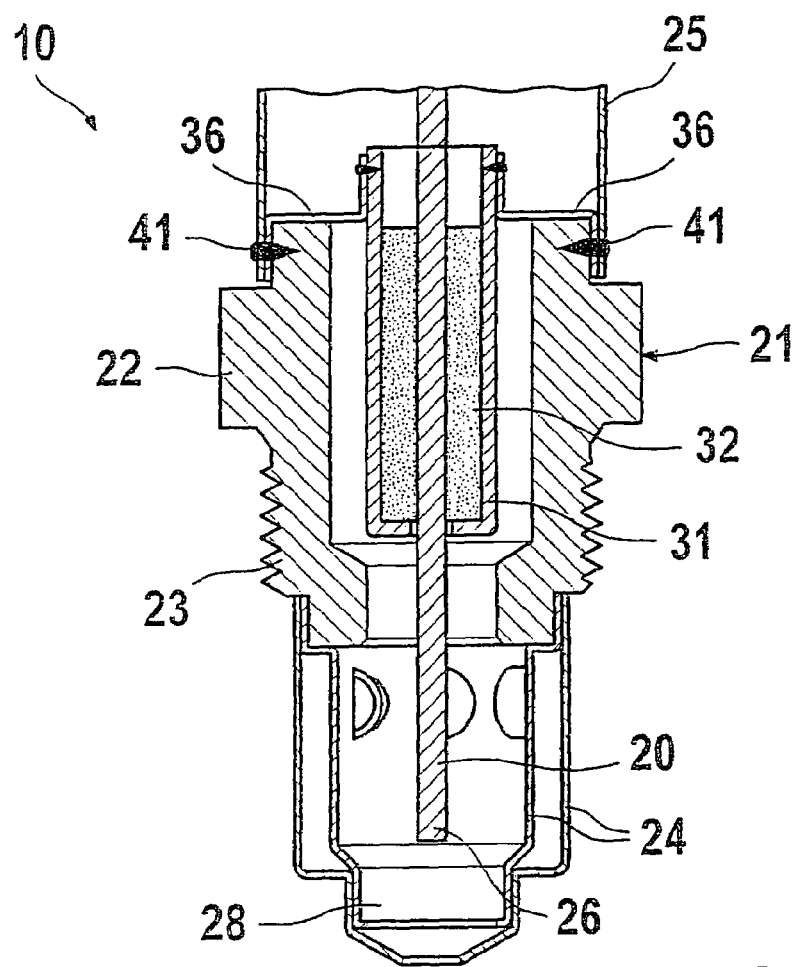
FIG. 3 shows a sectional view of a second exemplary embodiment of a gas sensor according to the present invention.

FIG. 3 shows a section of a gas sensor 10 as a second exemplary embodiment of the present invention. The second exemplary embodiment differs from the first exemplary embodiment according to FIG. 1 in the configuration of receptacle 31. Corresponding elements are designated in FIG. 3 by the same reference numerals as in FIG. 1. In the second exemplary embodiment, the space between sensor element 20 and the wall of cup-shaped receptacle 31 corresponds approximately to the height of sensor element 20 (i.e., to the extension of sensor element 20 in the direction perpendicular to its large surface), but at most to twice the height of sensor element 20. The shape of the wall of receptacle 31 largely corresponds to the form of sensor element 20, i.e., the wall cross section is rectangular. The edges of the wall are rounded.

In contrast to the first exemplary embodiment, receptacle 31 does not include a collar 34. An S-shaped metal connecting piece 36, which is affixed to metal receptacle 31 and to housing 21 by a welded connection 41, is provided to connect receptacle 31 to housing 21.

Figures 4A, 4B:
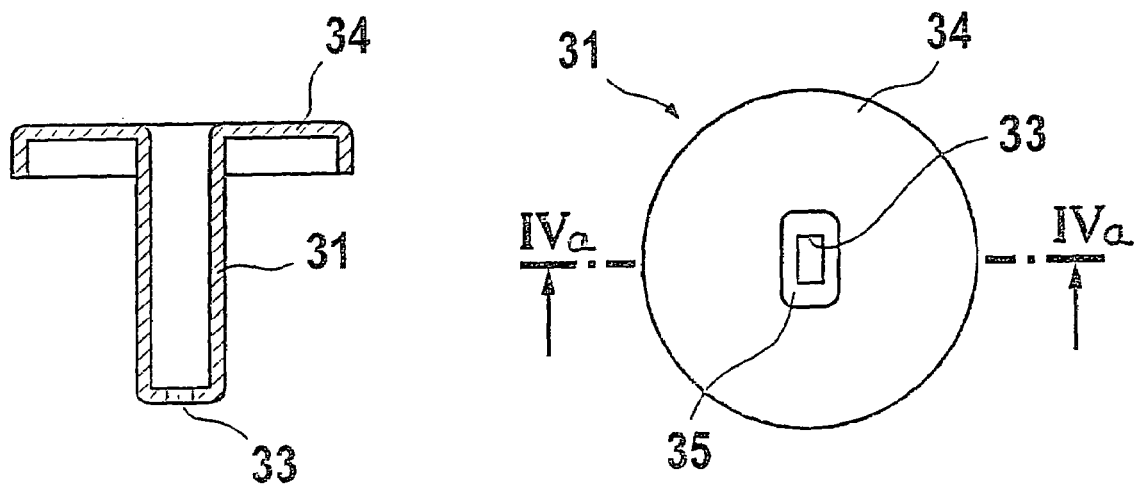

FIGS. 4a and 4b show a receptacle 31, which tightly encloses sensor element 20 as in the exemplary embodiment shown in FIG. 3, but which includes a collar 34 via which metal receptacle 31 is affixed to housing 21 via a welded connection as in the first exemplary embodiment.

FIGS. 5 through 8 show various exemplary embodiments of gas sensor 10, which differ from the first exemplary embodiment in the configuration of the sealing elements. Corresponding elements are designated in FIGS. 5 through 8 by the same reference numerals as in FIG. 1.

Figure 5:
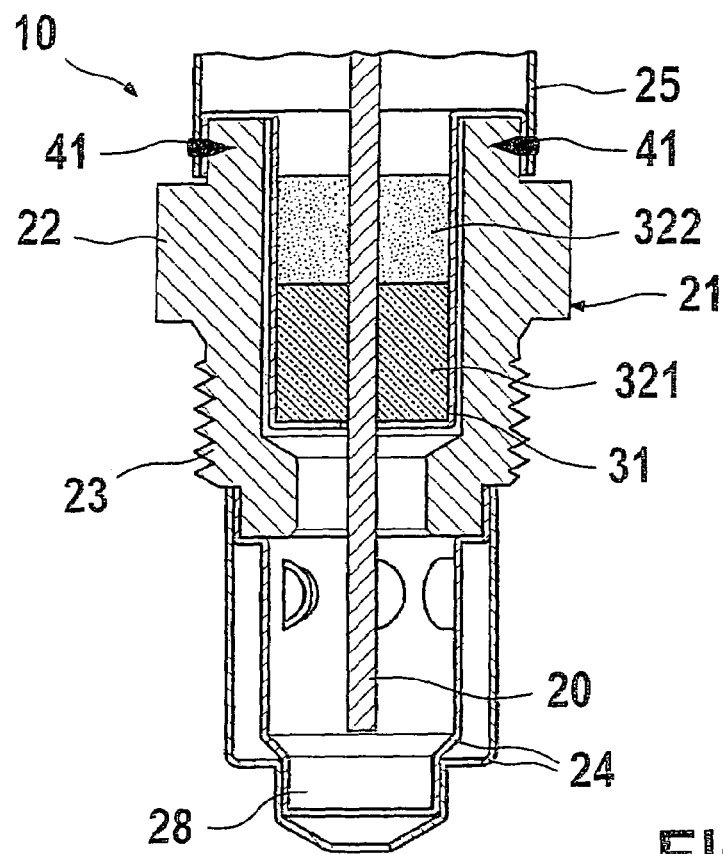
FIG. 5 shows a sectional view of a first embodiment of the first exemplary embodiment of the gas sensor according to the present invention.

In the exemplary embodiment according to FIG. 5, metal receptacle 31 includes a first sealing element 321 and a second sealing element 322, first sealing element 321 being on the side of metal receptacle 31 facing the measuring gas. The two sealing elements 321, 322 are made up primarily of a glass or a glass ceramic, the melting temperature of the glass of first sealing 321 element being above the temperature to which the composite of receptacle 31, first and second sealing elements 321, 322 and sensor element 20 is heated in order to fuse the glass of second sealing element 322. Thus, after production, second sealing element 322 is joined to housing 21 and sensor element 20 by a positive material connection, and seals sensor element 20 in housing 21 of gas sensor 10 with a gas-tight seal. The glass-forming component of first sealing element 321 is not completely melted on during production. This prevents the material of second sealing element 322 from being able to flow out of receptacle 31 during melting.

Figure 6:
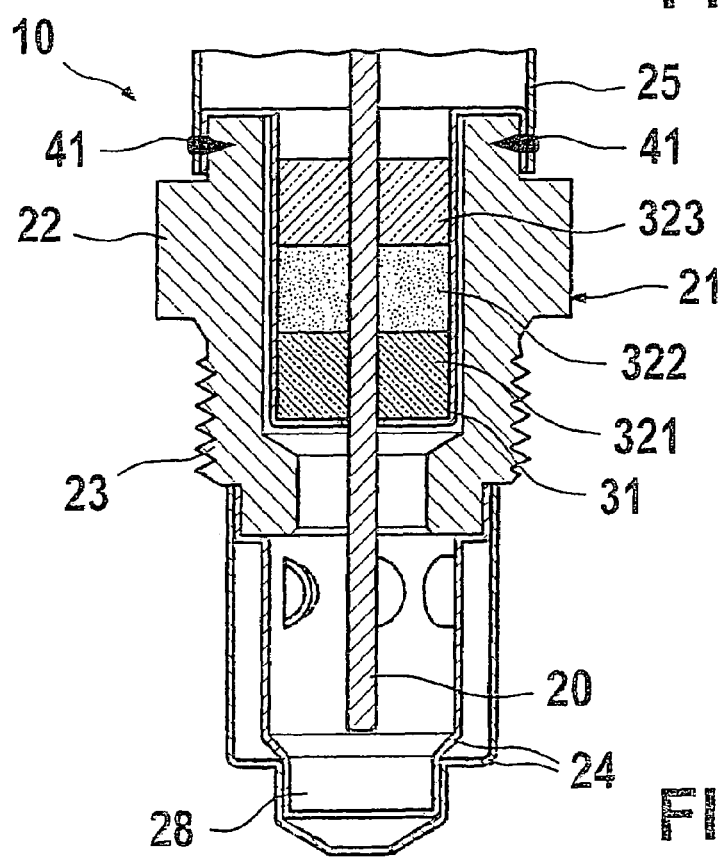
FIG. 6 shows a sectional view of a second embodiment of the first exemplary embodiment of the gas sensor according to the present invention.

The exemplary embodiment shown in FIG. 6 corresponds to the exemplary embodiment according to FIG. 5 and also includes a third sealing element 323 that is located on the side of second sealing element 322 facing away from the measuring gas. Third sealing element 323 includes a glass or a glass ceramic, and has the property of taking on a viscous consistency at the temperatures to which gas sensor 10 is exposed when used as intended.

Figure 7:
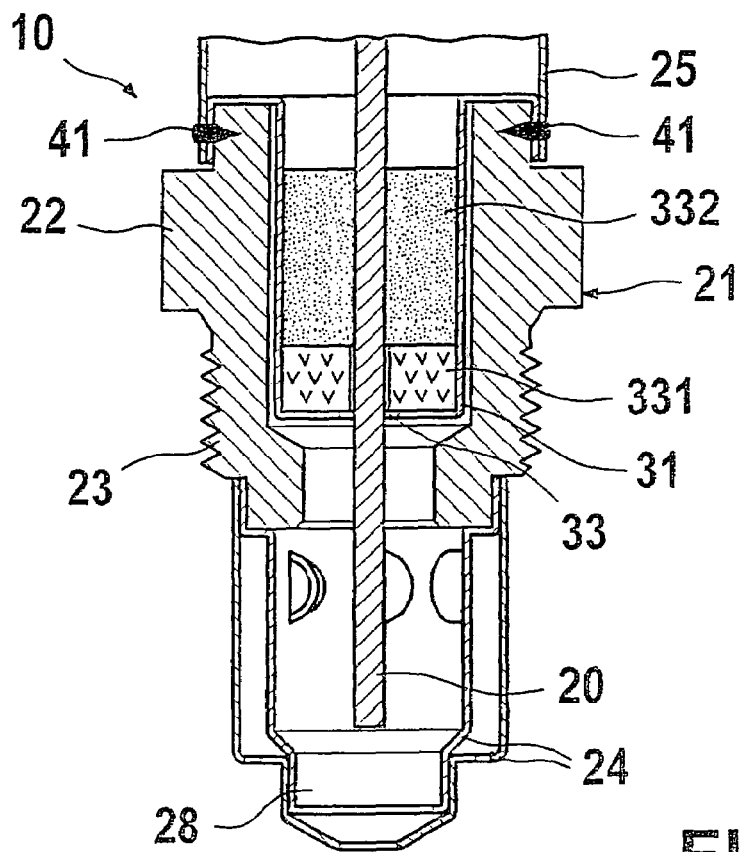
FIG. 7 shows a sectional view of a third embodiment of the first exemplary embodiment of the gas sensor according to the present invention.

In the exemplary embodiment according to FIG. 7, receptacle 31 includes a first sealing element 331 and a second sealing element 332, first sealing element 331 being on the side of receptacle 31 facing the measuring gas. First sealing element 331 is a sintered ceramic wafer including a recess for sensor element 20; as in the first and second exemplary embodiments, second sealing element 332 contains a glass or a glass ceramic. First sealing element 331 prevents the glass-forming component from flowing out of receptacle 31 during melting. In this exemplary embodiment, recess 33 for sensor element 20 has a broader configuration (the distance from the bottom of receptacle 31 to sensor element 20 corresponds for example to the height of sensor element 20), so that sensor element 20 may be introduced into recess 33 more easily.

Figure 8:
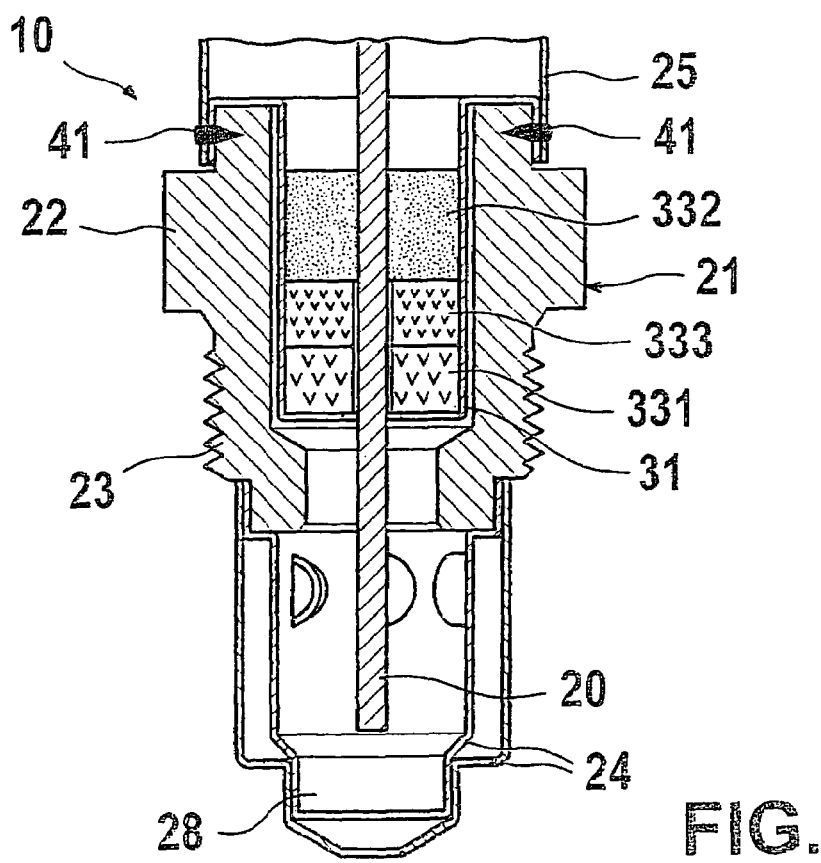
FIG. 8 shows a sectional view of a fourth embodiment of the first exemplary embodiment of the gas sensor according to the present invention.

The exemplary embodiment shown in FIG. 8 corresponds to the exemplary embodiment according to FIG. 7 and also contains a third sealing element 333 located between first and second sealing elements 331, 332. Third sealing element 333 is a wafer of pressed ceramic powdered material which also prevents the material of second sealing element 332 from flowing out during melting. In an additional exemplary embodiment, third sealing element 333 may replace second sealing element 332.

Additional exemplary embodiments of the present invention are produced by combining the exemplary embodiments according to FIG. 5 or 6 with the exemplary embodiments according to FIG. 7 or 8. Here sealing elements from one exemplary embodiment may be replaced by sealing elements from a different exemplary embodiment, or sealing elements from a different exemplary embodiment may be added.

Additional exemplary embodiments of the present invention provide that the sealing elements of the exemplary embodiments according to FIGS. 5 through 8, with their geometry adapted appropriately, are inserted into the receptacle of the second exemplary embodiment according to FIG. 3 or 4a and 4b.

What is claimed is:

1. A gas sensor for determining a physical property of a measuring gas, comprising:
   a sensor element arranged in a metal housing, the sensor element having a portion thereof which is exposed to the measuring gas, said portion being disposed on one side of an imaginary cross-sectional plane which is perpendicular to a longitudinal extension of the sensor element and which divides the sensor element substantially in half; and
   at least one sealing element which seals the sensor element and is arranged in a metal receptacle affixed to the metal housing;
   wherein the at least one sealing element surrounds the sensor element along the longitudinal extension of the sensor element one of at a centered position and on the half of the sensor element which is exposed to the measuring gas, the metal receptacle adjoins a measuring gas chamber, the metal receptacle is cup-shaped and has a closed configuration on one side, a bottom of the metal receptacle includes a recess for receiving the sensor element, an open end of the metal receptacle includes a section extending outward perpendicular to a longitudinal axis of the metal receptacle, a sleeve-shaped section is connected to the section, and a closed side of the receptacle juts out in front of a connection of the metal receptacle to the metal housing in a direction of the measuring gas chamber.

2. The gas sensor of claim 1, wherein the physical property includes one of a concentration of a gas component and a temperature of an exhaust gas.

3. The gas sensor of claim 1, wherein the sensor element is affixed in the metal housing by at least one of the at least one sealing element and the metal receptacle.

4. The gas sensor of claim 1, wherein the at least one sealing element is joined to the sensor element and the metal receptacle.

5. The gas sensor of claim 1, wherein the at least one sealing element includes one of a glass and a glass ceramic.

6. The gas sensor of claim 1, wherein a first expansion coefficient of the at least one sealing element and a second expansion coefficient of the sensor element differ by no more than 10 percent, the at least one sealing element is joined to the sensor element and the metal receptacle.

7. The gas sensor of claim 1, wherein the metal receptacle is affixed to the metal housing by an integral connection.

8. The gas sensor of claim 7, wherein the integral connection includes a welded connection.

9. The gas sensor of claim.1, wherein a sleeve surrounds a section of the sensor element and a contacting of the sensor element, the sleeve is arranged on a side of the gas sensor facing away from the measuring gas, and the metal receptacle and the sleeve are affixed to the metal housing by a common integral connection.

10. The gas sensor of claim 9, wherein the common integral connection includes a welded connection.

11. The gas sensor of claim 1, wherein a distance between the sensor element and a side wall of the metal receptacle is one of smaller than and equal to twice a height of the sensor element, the height of the sensor element is an extension of the sensor element perpendicular to a large surface of the sensor element.

12. The gas sensor of claim 1, wherein a first glass-containing sealing element and a second glass-containing sealing element are arranged in the metal receptacle one behind the other in a longitudinal direction of the sensor element, a glass of the first-containing sealing element facing the measuring gas has a higher melting point than a glass of the second sealing element facing away from the measuring gas, the glass of the second sealing element being completely molten after a heat treatment and forming an integral connection with the sensor element and the glass of the first sealing element is one of not molten and not completely molten.

13. The gas sensor of claim 1, wherein a first sealing element faces the measuring gas and a second sealing element faces away from the measuring gas are provided, the first sealing element and the second sealing element are arranged in the metal receptacle one behind the other in a longitudinal direction of the sensor element, the first sealing element being arranged on a side of the metal receptacle facing the measuring gas, and the first sealing element includes a ceramic and the second sealing element includes one of a glass and a glass ceramic.

14. The gas sensor of claim 13, wherein a third sealing element includes pressed ceramic powdered material and is arranged between the first sealing element and the second sealing element.

15. A gas sensor for determining a physical property of a measuring gas, comprising:
a sensor element arranged in a metal housing, the sensor element having a portion thereof which is exposed to the measuring gas, said portion being disposed on one side of an imaginary cross-sectional plane which is perpendicular to a longitudinal extension of the sensor element and which divides the sensor element substantially in half; and
at least one sealing element which seals the sensor element and is arranged in a metal receptacle affixed to the metal housing;
wherein the at least one sealing element surrounds the sensor element along the longitudinal extension of the sensor element one of at a centered position and on the half of the sensor element which is exposed to the measuring gas, a first glass-containing sealing element and a second glass-containing sealing element are arranged in the metal receptacle one behind the other in a longitudinal direction of the sensor element, a glass of the first-containing sealing element facing the measuring gas has a higher melting point than a glass of the second sealing element facing away from the measuring gas, the glass of the second sealing element being completely molten after a heat treatment and forming an integral connection with the sensor element, the glass of the first sealing element is one of not molten and not completely molten, and a glass-containing third sealing element, with a viscous consistency at temperatures at which the gas sensor is used, is arranged on a side of the second sealing element facing away from the measuring gas.

* * * * *